United States Patent
Weaver et al.

(10) Patent No.: US 10,036,877 B2
(45) Date of Patent: Jul. 31, 2018

(54) MICROLENS ARRAY FOR ENHANCED IMAGING OF MULTIREGION TARGETS

(71) Applicant: Vanderbilt University, Nashville, TN (US)

(72) Inventors: Charles David Weaver, Franklin, TN (US); Roger Bryan Greenway, Jr., Franklin, TN (US)

(73) Assignee: Vanderbilt University, Nashville, TN (US)

( * ) Notice: Subject to any disclaimer, the term of this patent is extended or adjusted under 35 U.S.C. 154(b) by 260 days.

(21) Appl. No.: 14/764,688

(22) PCT Filed: Feb. 5, 2014

(86) PCT No.: PCT/US2014/014881
§ 371 (c)(1),
(2) Date: Jul. 30, 2015

(87) PCT Pub. No.: WO2014/124015
PCT Pub. Date: Aug. 14, 2014

(65) Prior Publication Data
US 2015/0370061 A1    Dec. 24, 2015

Related U.S. Application Data

(60) Provisional application No. 61/760,976, filed on Feb. 5, 2013.

(51) Int. Cl.
*H04N 9/083* (2006.01)
*H04N 5/225* (2006.01)
(Continued)

(52) U.S. Cl.
CPC .......... *G02B 13/22* (2013.01); *G02B 3/0068* (2013.01); *G02B 7/006* (2013.01); *G02B 13/006* (2013.01);
(Continued)

(58) Field of Classification Search
CPC ......... G02B 5/08–5/10; G02B 26/0833; H01L 27/14627
(Continued)

(56) References Cited

U.S. PATENT DOCUMENTS 5,134,661 A * 7/1992 Reinsch ............... G06T 7/00
382/100
6,686,582 B1 2/2004 Volcker et al.
(Continued)

OTHER PUBLICATIONS

Orth et al., "Gigapixel Fluorescence Microscopy with a Water Immersion Microlens Array" Optics Express, vol. 21, No. 2, Jan. 2013, pp. 2361-2368.
(Continued)

*Primary Examiner* — Xi Wang
(74) *Attorney, Agent, or Firm* — Tarolli, Sundheim, Covell & Tummino LLP

(57) ABSTRACT

Systems and methods are provided for imaging a target as for example a multiwell plate. A plurality of regions of interest are selected on the target at a system control. The selected plurality of regions of interest are simultaneously imaged to provide an image with the plurality of regions of interest selectively magnified by a microlens array (30) and the regions that are not of interest are rejected by means of a mirrored aperture array, a mask, or selective illumination of the regions of interest of the target.

20 Claims, 3 Drawing Sheets

(51) Int. Cl.
  *G02B 13/22* (2006.01)
  *G02B 3/00* (2006.01)
  *G02B 21/00* (2006.01)
  *G02B 21/36* (2006.01)
  *G02B 21/16* (2006.01)
  *G06T 11/60* (2006.01)
  *G02B 7/00* (2006.01)
  *G02B 13/00* (2006.01)
  *G02B 27/10* (2006.01)
  *G02B 27/14* (2006.01)
  *G02B 27/30* (2006.01)
  *B01L 3/00* (2006.01)
  *G01N 21/25* (2006.01)
  *G01N 21/64* (2006.01)

(52) U.S. Cl.
  CPC ........... *G02B 21/008* (2013.01); *G02B 21/16* (2013.01); *G02B 21/367* (2013.01); *G02B 27/106* (2013.01); *G02B 27/141* (2013.01); *G02B 27/30* (2013.01); *G06T 11/60* (2013.01); *B01L 3/5085* (2013.01); *G01N 21/253* (2013.01); *G01N 21/6452* (2013.01)

(58) Field of Classification Search
  USPC ........ 348/222.1, 340, 291, 208.1; 250/208.1, 250/216, 226; 396/333
  See application file for complete search history.

(56) References Cited

U.S. PATENT DOCUMENTS

| | | | | |
|---|---|---|---|---|
| 7,009,652 | B1* | 3/2006 | Tanida | H01L 27/1462 348/291 |
| 7,259,917 | B2* | 8/2007 | Hillis | G06T 5/50 348/349 |
| 7,812,944 | B1 | 10/2010 | Schmidt | |
| 2004/0095477 | A1* | 5/2004 | Maki | G06K 9/3233 348/222.1 |
| 2004/0179834 | A1* | 9/2004 | Szajewski | G02B 3/0056 396/333 |
| 2004/0184155 | A1* | 9/2004 | Kornblit | G02B 27/0068 359/619 |
| 2008/0100899 | A1* | 5/2008 | Shimokawa | B81B 3/004 359/225.1 |
| 2009/0079824 | A1* | 3/2009 | Winsor | G01S 3/7864 348/143 |
| 2009/0185027 | A1* | 7/2009 | Cox | H04N 5/232 348/36 |
| 2010/0149210 | A1* | 6/2010 | Matsunaga | G06T 7/174 345/625 |
| 2010/0296367 | A1* | 11/2010 | Delprat-Jannaud | G01V 1/306 367/53 |
| 2014/0248693 | A1* | 9/2014 | Maher | G01N 21/6452 435/287.2 |

OTHER PUBLICATIONS

Schlingloff et al., "Microlenses as Amplification for CCD-Based Detection Devices for Screening Applications in Biology, Biochemistry, and Chemistry" Applied Optics, vol. 37, No. 10, Apr. 1998, pp. 1930-1934.

Eisner et al., "Confocal Microscopy with a Refractive Microlens-Pihnole Array" Optics Letters, vol. 23, No. 10, May 1998, pp. 748-749.

International Search Report corresponding to International Patent Application No. PCT/US2014/014881, 4 pages.

* cited by examiner

MICROLENS ARRAY FOR ENHANCED IMAGING OF MULTIREGION TARGETS

RELATED APPLICATIONS

This application is a national phase application of International Application No. PCT/US2014/014881 filed on Feb. 5, 2014, which claims priority to U.S. Provisional Patent Application No. 61/760,976, filed Feb. 5, 2013. The contents of both are hereby incorporated by reference herein.

TECHNICAL FIELD

This invention relates to imaging systems, and more particularly, to use of a microlens array for enhanced imaging of multiregion targets.

BACKGROUND

A lens is an optical device which transmits and refracts light, converging or diverging the beam. A simple lens consists of a single optical element, while a compound lens is an array of simple lenses with a common axis. Lenses are used as prosthetics for the correction of visual impairments such as myopia, hyperopia, presbyopia, and astigmatism. Many lenses used for other purposes have strict axial symmetry, whereas eyeglass lenses are only approximately symmetric. Lenses are also used in imaging systems, such as monoculars, binoculars, telescopes, microscopes, cameras, and projectors. Some of these instruments produce a virtual image when applied to the human eye, while others produce a real image which can be captured on photographic film or an optical sensor, or can be viewed on a screen. In these devices, lenses are sometimes paired up with curved mirrors to make a catadioptric system where the lens's spherical aberration corrects the opposite aberration in the mirror.

SUMMARY OF THE INVENTION

In accordance with an aspect of the present invention, a system includes a target and an imaging system configured to simultaneously image a plurality of regions of interest to provide an image. A microlens array is interposed between the target and the imaging system, and a region rejection component configured to prevent light reflected from non-ROI portions of the target from reaching the microlens array, the microlens array and the region rejection component being configured to reflect light incident on the lens at an angle greater than a predetermined value. The mirrored aperture array and the microlens array are configured to selectively magnify the content of a plurality of regions of interest such that, within the image, at least one region that is not of interest is substantially replaced by the magnified content of the plurality of regions of interest.

In accordance with another aspect of the present invention, a method is provided for imaging a target. A plurality of regions of interest are selected on the target at a system control. The selected plurality of regions of interest are simultaneously imaged to provide an image with the plurality of regions of interest selectively magnified such that at least one region that is not of interest is substantially replaced by the magnified plurality of regions of interest.

In accordance with yet another aspect of the present invention, a system is provided for imaging a target. The system includes a multiwall plate having a plurality of wells separated by walls. An imaging system is configured to simultaneously image a plural subset of the plurality of wells to provide an image. A microlens array, interposed between the multiwall plate and the imaging system, is configured to selectively magnify the content of the plurality of wells such that, within the image, the walls are substantially replaced by the magnified content of plural subset of the wells.

DETAILED DESCRIPTION

In many scientific imaging applications, a collection of objects are imaged simultaneously. In other words, a single image is taken which includes multiple objects of interest as well as all of the space around and between the individual objects. The image can be considered to be made up of a contiguous map of regions-of-interest (ROIs) and non-ROIs. The ROI fill factor (FF) of the image is defined here as the ratio of the total image area inside the collective ROIs ($\Sigma$ROI) to the total area of the image ($IA_{TOT}$).

$$FF=[\Sigma ROI]/[IA_{TOT}] \qquad \text{Eq. 1}$$

The ROI fill factor can range in value from 0 to 1, depending upon the number, size, and relative spacing (or the sparseness) of the ROI population in the image. For pixilated imaging sensors, this would translate to the ratio of the total number of pixels that fall inside an ROI to the total number of pixels in the sensor. When the primary intent of the image is to capture information about the ROIs and the ROI fill factor is something less than one (1.0), a certain percentage of the image contains no information of interest, corresponding to an underutilization of the sensor's pixels.

In accordance with an aspect of the present invention, a microlens array is used to image a target at high resolution, such that for a given image of the target, at least a portion of the target is magnified at the expense of another portion of the target. In one implementation, the target can include ROIs and non-ROIs, and the microlens array can be configured to magnify the ROIs as to exclude some or all of the regions that are not of interest. In another implementation, the entire target may be of interest. In such a case, a series of images can be taken, with each image having designated ROIs, such that each image excludes part of the target to magnify the arbitrary ROIs. Either the target, the microlens array, a region restriction component restricting reflected light from the non-ROIs, or the imager can be rotated or translated (including vertically "in Z") such that every portion of the target is a designated ROI in at least one image. The series of images can then be stitched together via appropriate image stitching software to provide a high resolution composite image.

Figure 1:
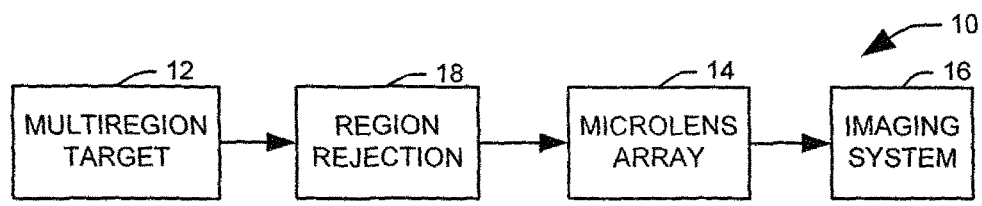
FIG. 1 illustrates a system for imaging a target in accordance with an aspect of the present invention.

FIG. 1 illustrates a system 10 for imaging a target 12 in accordance with an aspect of the present invention. The system 10 includes a microlens array 14 positioned and configured to magnify the multiple regions of interest on the target 12 onto an imaging system 16. It will be appreciated that the regions of interest can be either natural (e.g., wells in a microplate assembly) or relatively arbitrary and selected by an operator or a system control via alignment of one of the target 12, the microlens array 14, or the imaging system 16. Also, additional optical components (not shown) can be included in an optical path between the target 12 and the imaging system 16, including but not limited to lenses, filters, diffraction gratings, polarizers, and masks. Similarly, the system 10 can include a light source (not shown), for example, within the visible, infrared, or ultraviolet range to illuminate the target 12, induce fluorescence or phosphorescence in the target, or other facilitate imaging of the regions of interest.

In accordance with an aspect of the present invention, the system includes a region rejection component 18, configured to restrict light reflected from non-ROI portions of the target from reaching the microlens array 14, For example, in one implementation, the rejection component 18 can include a mirrored aperture array comprising a mirrored surface with apertures corresponding to the microlenses in the microlens array 14 positioned just before the microlens array prevent light incident on the microlens array 14 at an angle greater than a predetermined value from reaching the array, In another implementation, the region rejection component 18 can include a mask interposed between the microlens array 14 and the target 12. In yet another implementation, the region rejection component 18 can include a light source configured to selectively illuminate the regions of interest of the target 12. Regardless of the specific nature of the region rejection component 18, the region rejection component and the microlens array 14 are positioned and configured to selectively magnify regions of interest at the target 12, such that, within the image of the target, the portions of the target outside of the regions of interest are substantially replaced with portions of the target within the regions of interest. It will be appreciated that the efficiency of the system is greatly enhanced when the regions on interest on the target are distributed in an orderly fashion, such as an array, allowing the microlens array 14 to utilize identical or substantially similar microlens assemblies throughout a regular array. It will be appreciated, however, that the microlens array can be irregular, as opposed to evenly spaced and orderly, particularly where helpful in matching the individual microlenses to known locations on a particular target type. Further, a given lens in a microlens array 14 may have identical or different optical characteristics, such as magnification.

In one implementation, the microlens array 14 is configured to operate with a microwell plate, for example, a three hundred eighty-four well assay plate. The microlens array 14 can be positioned such that each lens magnifies an arbitrary portion of the well, with the remainder of the well and the wails surrounding the well are rejected in the image. In one implementation, this can allow for imaging of single cells within a given assay. This approach can be of particular value in a kinetic imaging plate reader application, as the imaging in these systems tends to be time sensitive, requiring multiple images to be taken over time. The microlens array 14 allows this imaging to be done in parallel, greatly decreasing the time necessary for each image. Accordingly, changes at the level of an individual cell in multiple ROIs dispersed over a large field (e.g., simultaneously in all wells of a microplate) can be tracked with an enhanced temporal resolution.

In another implementation, each well can have multiple regions of interest. For example, the multiple regions of interest may be a plurality of intracellular sub-structures, such as mitochondria, a portion of the well containing a particular type of cell or a plurality of cells recognized as interesting by its size, shape, or other characteristics, or it simply may be the area of the image where there are cells and not the area of the image where there are not cells. In one implementation, the region of interest can further include a reference region that does not contain cells for use in detecting cell-dependent changes in the other regions of interest.

In the plate reader implementation, the microlens assembly can have three-hundred eighty-four microlenses, arranged to correspond with the wells within the assay plate. It will be appreciated that the microlens array can include additional microlenses that are not aligned with associated microwells, for example, to allow for manufacturing tolerances on the edge of the array. In this implementation, the microlens array 14 can be implemented as a regular, rectangular array, that is, an array having evenly-spaced and orderly rows and columns. It will be appreciated, however, that for other applications, the microlens array 14 can be made to be a non-rectangular and/or an irregular array. For example, a system 10 in accordance with the aspect of the present invention could be used in astronomy, machine vision, light field photography, and any of a number of other imaging applications.

In another implementation, the system 10 can be used with planar patch-clamp chips to add an imaging aspect to the process. Since the apertures in glass chips use for planar patch-clamp techniques can be regularly spaced, they can be readily adapted to imaging with the microlens array of the current invention. In one example, each microlens on the array is matched with one of the apertures on the glass chip. In another example, a plurality of apertures, for example, a group of sixty-four, can be imaged through each microlens. In another application, the target 12 could include micropatterns that are printed with regular spacing in the wells of microwell plates or any other kind of relevant substrate. These micropatterns may be used to encourage attachment of cells or other objects in a regularly spaced array, with the microlens array 14 configured to selectively magnify the expected points of attachment. A non-exhaustive list of other applications can include next generation sequencing applications, protein and nucleic acid microarray analysis, electrophorectic gel and blot analysis, and whole animal imaging.

Figure 2:
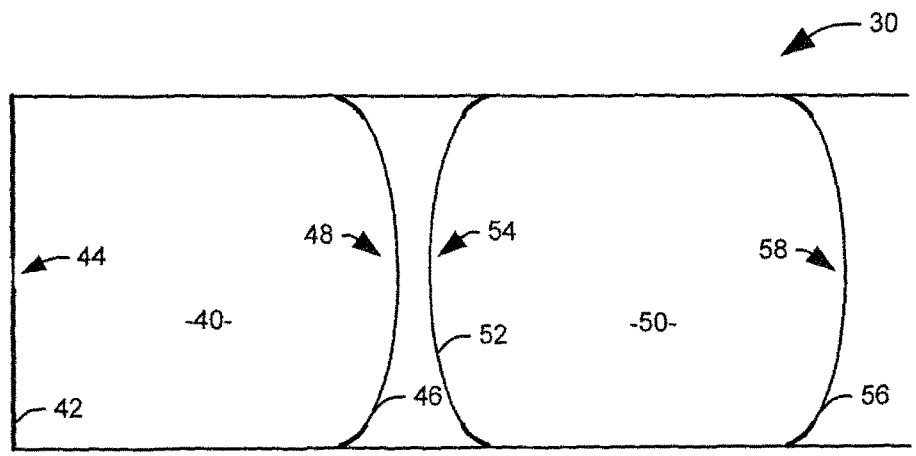
FIG. 2 illustrates one example of a microlens assembly that could be found in a microlens array in accordance with an aspect of the present invention.

FIG. 2 illustrates one example of a microlens assembly 30 that could be found in a microlens array in accordance with an aspect of the present invention. The assembly includes two optical elements, a plano-convex element 40 and a biconvex element 50. A plano surface 42 of the plano-convex element 40 is chrome coated and includes a square aperture 44 at its center. The plano surface 42 has an aperture pitch on the order of five hundred micrometers in diameter, and the square aperture 64 is approximately forty-two micrometers. A convex surface 46 of the plano-convex element 40 has a diameter of five-hundred micrometers, with a clear, central aperture 48 of approximately four hundred twenty-five micrometers. A conic constant of the convex surface 46 is approximately −0.74, and the radius of curvature is on the order of 681.7 micrometers. A sag of the entire convex surface 46 is around 46.3 micrometers, and a sag of the clear aperture 48 is approximately 33.3 micrometers. The plano-convex element 40 is approximately seven hundred forty-five micrometers thick between the two surfaces 42 and 46.

A first convex surface 52 of the biconvex element 50 has a diameter of five-hundred micrometers, with a clear, central aperture 54 of approximately four hundred twenty-five micrometers. A conic constant of the first convex surface 52 is approximately −0.74, and the radius of curvature is on the order of 681.7 micrometers. A sag of the entire first convex surface 52 is around 46.3 micrometers, and a sag of the clear aperture 54 is approximately 33.3 micrometers. A second convex surface 56 of the biconvex element 50 has a diameter of five-hundred forty micrometers, with a clear, central aperture 58 of approximately four hundred sixty micrometers. A conic constant of the second convex surface 56 is approximately −3.59, and the radius of curvature is on the order of 784.5 micrometers. A sag of the entire second convex surface 56 is around 43.4 micrometers, and a sag of the clear aperture 58 is approximately 32 micrometers. The biconvex element 50 is approximately seven hundred forty-five micrometers thick between the two surfaces 52 and 56.

Figure 3:
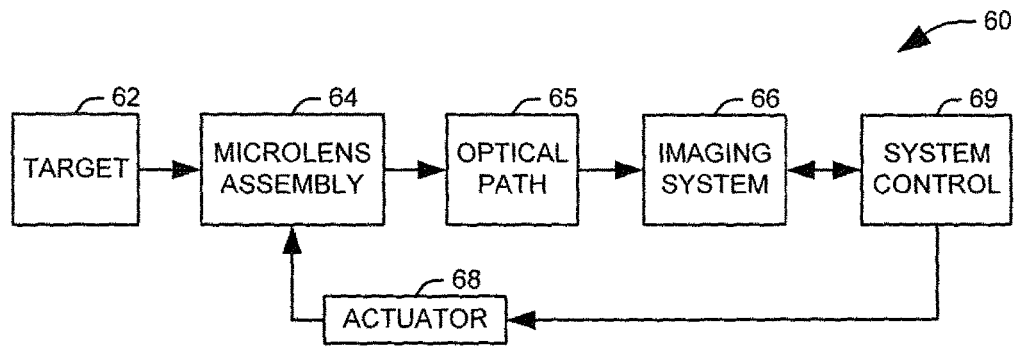
FIG. 3 illustrates a first example of a system for imaging a target in accordance with an aspect of the present invention.

It will be appreciated that the microlens array 14 can be configured in various ways according to a desired application. In one implementation of an imaging system 60, illustrated as FIG. 3, a microlens assembly 64, comprising a microlens array and a mirrored aperture array, is positioned between the target 62 and the other optical components 65 in the optical path. In one implementation, the optical components 65 can include a telocentric lens assembly. This arrangement allows data to be collected from a smaller, higher magnification field of view in the desired portion of the well being imaged.

In the case where a larger field of view is required, one of the target 62, the microlens assembly 64, and the imager 66 can be translated or rotated slightly along one or more of the axis normal to the target and the axes defining a plane perpendicular to the normal axis. For example, an actuator 68, controlled by a system control 69, can be used to move one or more of the target 62, the microlens assembly 64, and the imager 66, and a series of images can be taken and then combined using imaging stitching software at the system control 69 to form a high resolution composite image. In the illustrated example, the actuator 68 is configured to rotate and translate the microlens assembly 64.

In one implementation, this is done as part of a virtual focusing arrangement. Automated microscopes require the use of mechanical autofocusers. These autofocusers are slow and in many case imprecise and as such both limit the throughput and quality of images acquired with automated microscopes. This is particularly true when considering biological targets that have relatively large depth/thickness (e.g., cell colonies, zebrafish embryos, C. elegans). To this end, the system control 69 can instruct the actuator 68 to move the microlens assembly 64 in a predetermined pattern of translations and rotations that define a search space for the virtual focusing. The resulting series of images is then reviewed, for example, via an edge finding algorithm, for segments that are within focus, and a composite image is generated from the segments determined to be in focus. Computer-based autofocusing can be made massively parallel much less expensively that automated microscopes and it much less risk-prone since mistakes in autofocusing do not require reimaging, only reanalysis.

Figure 4:
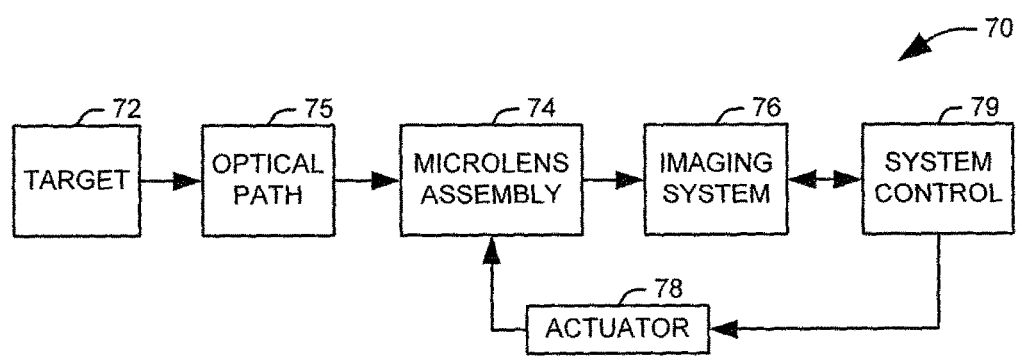
FIG. 4 illustrates a second example of a system for imaging a target in accordance with an aspect of the present invention.

In another implementation, represented in FIG. 4, a microlens assembly 74, comprising a microlens array and a mirrored aperture array is implemented near a sensor 76 instead of between the optics 75 and the target 72. As with the system of FIG. 3, an actuator 78, controlled by a system control 79, can be used to move one or more of the target 72, the microlens array 74, and the imager 76, and a series of images can be taken and then combined using imaging stitching software at the system control 79 to form a high resolution composite image. In the illustrated implementation, the system control 79 can instruct the actuator 78 to progress through a search space, comprising a series of translations and/or rotations of the array 74, imager 76, or target 72, that comprehensively covers the target 72, or at least a known region of interest on the target that is larger than can be imaged in a single image at a desired level of magnification. For each of these images, a nominal region of interest is a location picked by the system control 79 at each step in the search space, and an image is taken to magnify that region of interest at the expense of the surrounding portion of the target 72. The resulting series of images is stitched together to produce a composite image having the resolution at or near that of a single image through the microlens array, but covering the entire target or known region of interest. In one application, the search pattern can be repeated in cycles to provide multiple composite images as frames in a video to view the target 72 over time. For example, the images be used to track cells movements, for instance, or pixel values can be extracted from regions of interest in these images and the variation in the pixel values frame-to-frame will used to construct waves.

Another application for the camera face microlens array is an Imaging Mapping Spectrometer (IMS) system. More and more biological experiments seek to interrogate multiple markers simultaneously or to determine where and when two markers come close to one another (e.g., two proteins contacting each other in a cell), Often these markers spectrally overlap one another which can make discriminating one from the other difficult. In addition, presently available imaging plate readers require mechanical filters changers that limit the speed and flexibility of the system. The proposed format could greatly extend the utility of both IMS and the types of experiments achievable with an imaging plate reader in combination with computational techniques like linear unmixing.

Figures 5, 6:
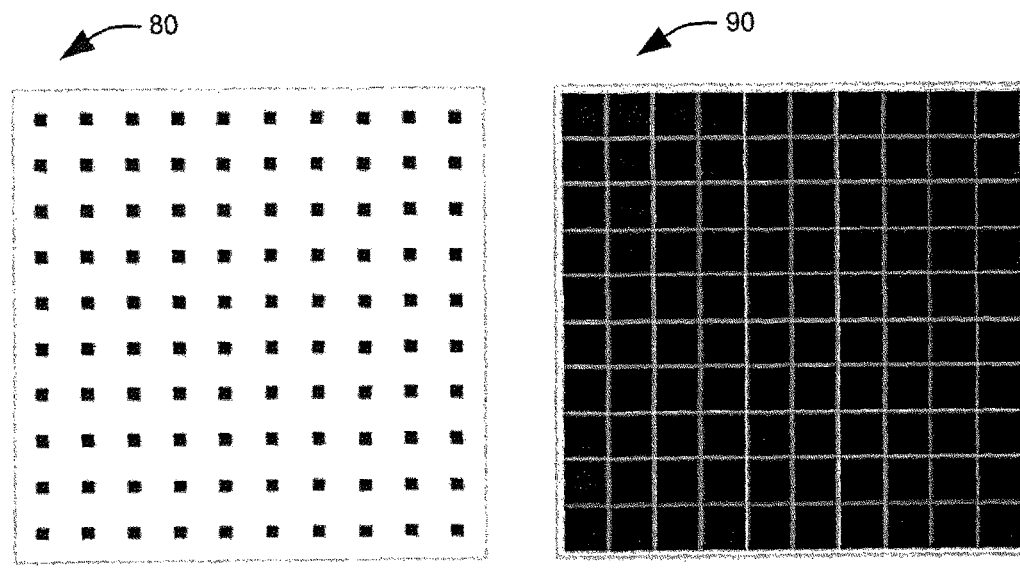
FIG. 5 illustrates one example of a target as it might appear without the selective magnification of a microlens array.
FIG. 6 illustrates an example of an image taken of the target through the microlens array.

FIG. 5 illustrates one example of a target 80 as it might appear without the selective magnification of a microlens array. In the illustrated implementation, the target 80 is a microwell plate having a plurality of microwells separated by plate walls. It will be appreciated that the microwells contain regions of interest, for example, regions likely to contain specimens, and regions that are not of interest, which can include portions of the well less likely to contain specimens as well as the plate walls. In FIG. 5, regions of interest are shown in black, and regions that are not of interest, including at least the microwell walls, are shown in white. FIG. 6 illustrates an example of an image 90 taken of the target through the microlens array. It will be appreciated that the regions of interest is greatly expanded at the expense of the regions that are not of interest.

Figure 7:
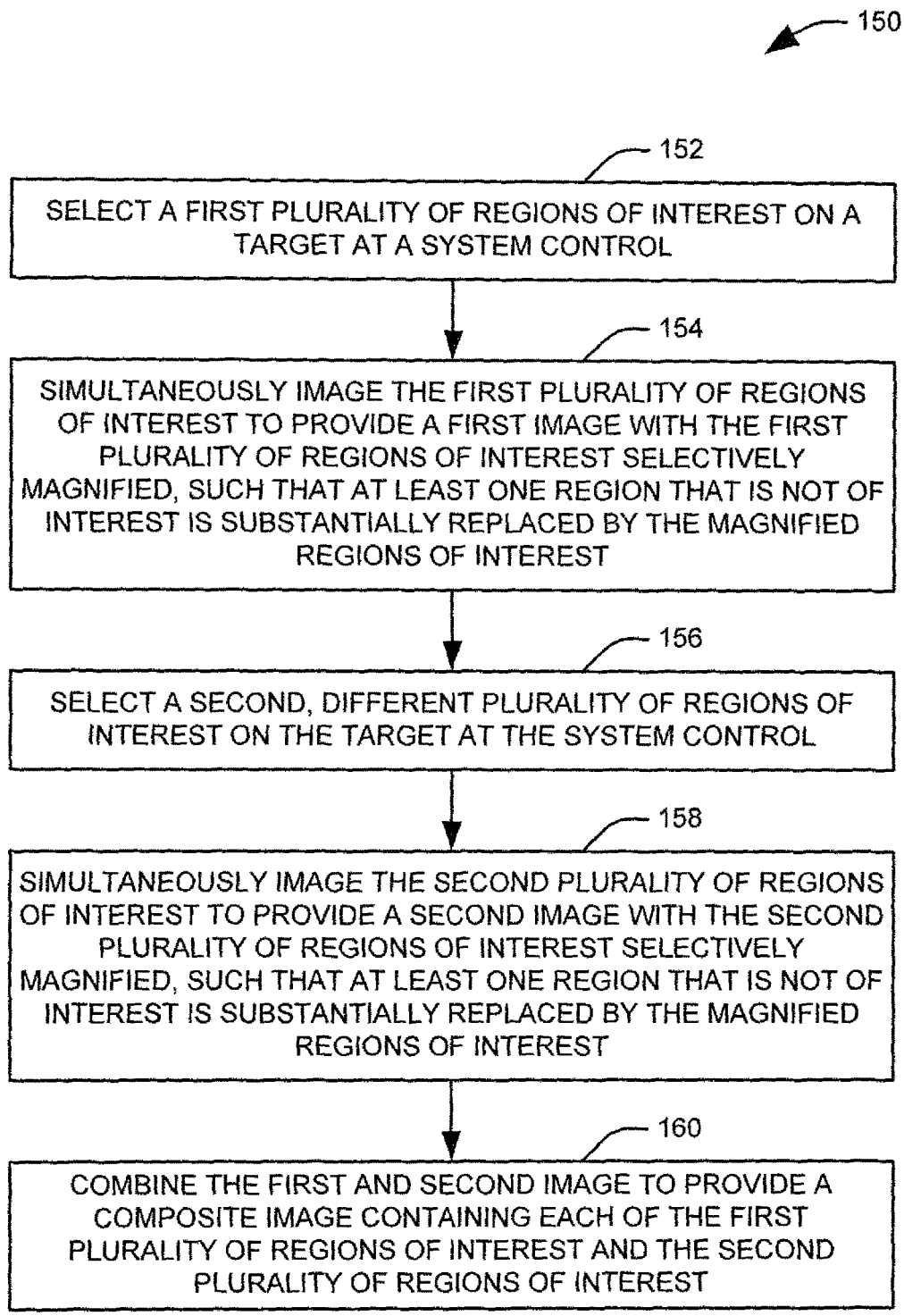
FIG. 7 illustrates a method for imaging a target in accordance with an aspect of the present invention.

In view of the foregoing structural and functional features described above, a methodology in accordance with various aspects of the present invention will be better appreciated with reference to FIG. 7. While, for purposes of simplicity of explanation, the methodology is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention. The various acts of the method depicted in FIG. 7 can be executed automatically such as via a processor, computer, and/or controller configured with executable instructions to carry out the various acts described herein. Moreover, discrete circuit control implementations are possible in addition to hybrid controls that include both discrete and integrated circuit processing elements.

FIG. 7 illustrates a method 150 for imaging a target in accordance with an aspect of the present invention. At 152, a first plurality of regions of interest on the target are selected at a system control. At 154, the first plurality of regions of interest are simultaneously imaged to provide a first image with the first plurality of regions of interest selectively magnified, such that at least one region that is not of interest is substantially replaced by the magnified first plurality of regions of interest. At 156, a second, different plurality of regions of interest on the target are selected at the system control. For example, a system control can instruct an actuator to perform rotations and/or translations of either the target or the imaging system, such that the selective magnification provided by a microlens array is changed to the new regions of interest.

At 158, the second plurality of regions of interest are simultaneously imaged to provide a second image with the second plurality of regions of interest selectively magnified such that at least one region that is not of interest is substantially replaced by the magnified second plurality of regions of interest. At 160, the first image and the second image are combined into a high resolution composite image including each of the first plurality of region of interest and the second plurality of regions of interest. For example, the images can be combined via an appropriate image stitching algorithm.

Figure 8:
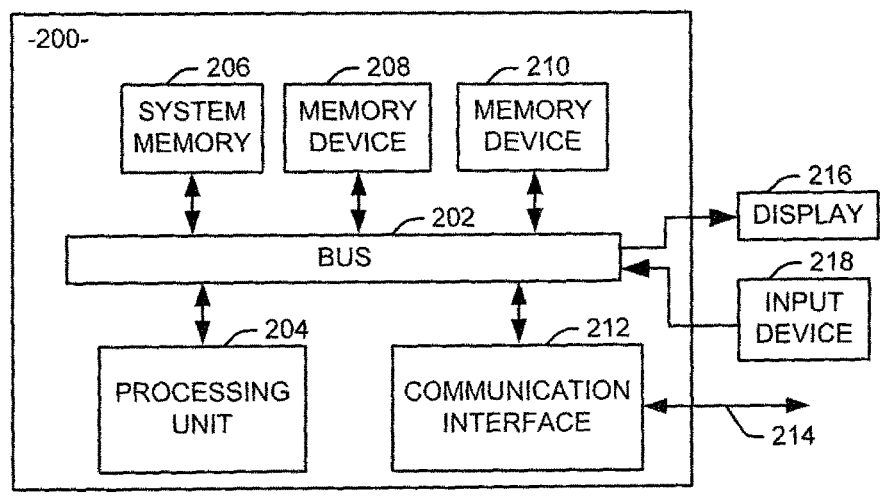
FIG. 8 is a schematic block diagram illustrating an exemplary system of hardware components capable of implementing examples of the systems and methods disclosed herein, such as the imaging system described previously.

FIG. 8 is a schematic block diagram illustrating an exemplary system 200 of hardware components capable of implementing examples of the systems and methods disclosed herein, such as the imaging system described previously. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can include a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard, touch screen, and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an imaging system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A system comprising
a target comprising a plurality of regions of interest and at least one region that is not of interest;
an imaging system that images the target as to simultaneously image the plurality of regions of interest to provide an image; and
a microlens array, interposed between the target and the imaging system; and
a region rejection component that prevents light reflected from the at least one region that is not of interest of the target from reaching the microlens array, the microlens array and the region rejection component being configured to selectively magnify contents of the plurality of regions of interest such that, within the image, the at least one region that is not of interest is substantially replaced by a portion of the magnified contents of the plurality of regions of interest.

2. The system of claim 1, wherein the target includes a multiwell plate having a plurality of wells, separated by walls, the plurality of regions of interest each including at least a portion of a well of the plurality of wells, and the at least one region that is not of interest includes the walls separating the plurality of wells.

3. The system of claim 1, wherein the plurality of regions of interest is a proper subset of a set of regions of interest associated with the target.

4. The system of claim 3, further comprising a system control configured to select the proper subset of the plurality of regions of interest on the target for imaging.

5. The system of claim 1, the microlens array comprising a plurality of discrete microlens components, each of the discrete microlens components comprising a doublet lens assembly.

6. The system of claim 5, each doublet lens assembly comprising a first, plano-convex assembly having a planar surface facing a well of the plurality of wells and a second, biconvex assembly configured to direct a magnified representation of the plurality of regions of interest to the imaging system.

7. The system of claim 1, further comprising an actuator configured to perform at least one of a rotation and a translation of a selected one of the target and the imaging system.

8. The system of claim 7, the imaging system being configured to capture a series of images during the at least one of the rotation and the translation of the selected one of the target, and the imaging system and combine the images into a composite image using a system control of the system.

9. The system of claim 8, wherein the system control is configured to take a first image of a region of the target containing a subject of interest, and a second image of a reference image of the target that does not contain the subject of interest.

10. The system of claim 8, wherein the system control is configured to capture the series of images that each cover a selected plurality of regions of interest of the target, the selected plurality of regions of interest associated with each of the series of images being selected such that the composite image covers substantially all of the target.

11. The system of claim 8, wherein the system control is configured to locate portions of the target within each of the series of images that are in focus via an edge finding algorithm, the composite image being formed using the located portions of the target in each of the series of images.

12. The system of claim 1, wherein the microlens array is a regular array which is arranged in rows and columns.

13. The system of claim 1, wherein the region rejection component comprises a mirrored aperture array, interposed between the microlens array and the target.

14. The system of claim 1, wherein the target includes a planar patch-clamp chip having a plurality of apertures, each of the plurality of regions of interest includes at least one aperture.

15. The system of claim 1, further comprising at least one optical component positioned between the target and the microlens array along an optical axis of the system.

16. A method for imaging a target using a system that includes an imaging system comprising: selecting a first plurality of regions of interest on the target using a system control of the system; and simultaneously imaging the selected first plurality of regions of interest of the target to provide a first image with the first plurality of regions of interest being selectively magnified such that at least one region that is not of interest of the target is substantially replaced by a portion of magnified the first plurality of regions of interest;

selecting a second plurality of regions of interest on the target using the system control of the system, the second plurality of regions of interest being different than the first plurality of regions of interest;

simultaneously imaging the second plurality of regions of interest to provide a second image with the second plurality of regions of interest being selectively magnified such that at least one region that is not of interest is substantially replaced by a portion of magnified the second plurality of regions of interest; and combining the first image and the second image into a composite image including each of the first plurality of region of interest and each of the second plurality of regions of interest.

17. The method of claim 16, wherein selecting the second plurality of regions of interest using the system control of the system comprises instructing an actuator to perform at least one of a rotation and a translation of a selected one of the target and the imaging system.

18. A system comprising
a multiwell plate having a plurality of wells separated by walls; an imaging system configured to simultaneously image a plural subset of the plurality of wells to provide an image; and
a microlens array, interposed between the multiwell plate and the imaging system and configured to selectively magnify contents of the plurality of wells such that, within the image, the walls are substantially replaced by a portion of the magnified contents of the plural subset of the plurality of wells.

19. The system of claim 18, further comprising an actuator configured to perform at least one of a rotation and a translation of a selected one of the target and the imaging system, the imaging system being configured to capture a series of images during the at least one of the rotation and the translation of the selected one of the target and the imaging system and combine the images into a composite image using a system control of the system.

20. A system comprising a target, wherein the target comprising a plurality of regions of interest and at least one region that is not of interest;
an imaging system configured to simultaneously image the plurality of regions of interest to provide an image; and
a microlens array, interposed between the target and the imaging system, with a first microlens in the microlens array providing a first magnification and a second microlens in the microlens array providing a second magnification different than the first magnification; and
a region rejection component configured to prevent light reflected from the at least one region that is not of interest of the target from reaching the microlens array, the microlens array and the region rejection component being configured to selectively magnify contents of the plurality of regions of interest such that, within the image, the at least one region that is not of interest is substantially replaced by a portion of magnified contents of the plurality of regions of interest.

* * * * *